US011992267B2

(12) United States Patent
Ueno et al.

(10) Patent No.: US 11,992,267 B2
(45) Date of Patent: *May 28, 2024

(54) OPHTHALMOLOGIC APPARATUS AND OPHTHALMOLOGIC SYSTEM

(71) Applicant: TOPCON CORPORATION, Tokyo (JP)

(72) Inventors: Shingo Ueno, Tokyo (JP); Ryousuke Ito, Tokyo (JP)

(73) Assignee: TOPCON CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/190,032

(22) Filed: Mar. 24, 2023

(65) Prior Publication Data

US 2023/0233079 A1 Jul. 27, 2023

Related U.S. Application Data

(63) Continuation of application No. 16/937,626, filed on Jul. 24, 2020, now Pat. No. 11,642,024.

(30) Foreign Application Priority Data

Jul. 30, 2019 (JP) ................................. 2019-139397

(51) Int. Cl.
*A61B 3/15* (2006.01)
*A61B 3/16* (2006.01)

(52) U.S. Cl.
CPC ............... *A61B 3/152* (2013.01); *A61B 3/16* (2013.01)

(58) Field of Classification Search
CPC .................................. A61B 3/152; A61B 3/16
(Continued)

(56) References Cited

U.S. PATENT DOCUMENTS

| 3,452,589 A * | 7/1969 | Hargens ............ A61B 3/16 600/398 |
| 2004/0044333 A1* | 3/2004 | Sugiura ............ A61F 9/00817 606/4 |

(Continued)

FOREIGN PATENT DOCUMENTS

| JP | 2005287782 A | 10/2005 |
| JP | 2010264020 A | 11/2010 |

(Continued)

OTHER PUBLICATIONS

Notice of Reasons for Refusal dated Feb. 28, 2023 in connection with Japanese Patent Application No. 2019-139397, 9 pgs. (including translation).

(Continued)

*Primary Examiner* — Sharrief I Broome
(74) *Attorney, Agent, or Firm* — Chiesa Shahinian & Giantomasi PC

(57) ABSTRACT

An ophthalmologic apparatus includes: a head unit having an optical system capable of receiving light reflected from a subject's eye; a drive mechanism that movably holds the head unit; an alignment detection unit that detects a position of the subject's eye relative to the head unit; and a control unit that controls the drive mechanism. The drive mechanism includes at least two arms rotatably connected together, at least two first rotation support mechanisms and at least three second rotation support mechanisms which allow the head unit to move, and at least five driving units for driving the rotation support mechanisms. The control unit is capable of controlling the driving units using a measurement result of the alignment measuring unit to align the head unit and the subject's eye with each other.

11 Claims, 12 Drawing Sheets

(58) Field of Classification Search
USPC .......................................................... 351/208
See application file for complete search history.

(56) References Cited

U.S. PATENT DOCUMENTS

| | | | | |
|---|---|---|---|---|
| 2005/0275804 | A1* | 12/2005 | Masaki | A61B 3/152 |
| | | | | 351/208 |
| 2015/0115515 | A1* | 4/2015 | Takahashi | B23Q 1/03 |
| | | | | 901/49 |
| 2015/0272436 | A1* | 10/2015 | Hayashi | A61B 3/107 |
| | | | | 351/208 |
| 2018/0092705 | A1 | 4/2018 | Ootsuki et al. | |
| 2023/0233079 | A1* | 7/2023 | Ueno | A61B 3/16 |
| | | | | 351/208 |

FOREIGN PATENT DOCUMENTS

| | | | |
|---|---|---|---|
| JP | 2013172786 | A | 9/2013 |
| JP | 2017093977 | A | 6/2017 |
| JP | 2017144125 | A | 8/2017 |
| JP | 2018042760 | A | 3/2018 |
| JP | 2018051337 | A | 4/2018 |
| JP | 2019058618 | A | 4/2019 |
| WO | 2017169135 | A1 | 5/2017 |

OTHER PUBLICATIONS

Notice of Reasons for Refusal dated Dec. 26, 2023 in connection with Japanese Application No. 2023-067765, 6 pgs. (including translation).

* cited by examiner

OPHTHALMOLOGIC APPARATUS AND OPHTHALMOLOGIC SYSTEM

CROSS-REFERENCE TO RELATED APPLICATION

This application is a Continuation of prior-filed U.S. Utility patent application Ser. No. 16/937,626, filed Jul. 24, 2020, which claims priority to Japanese Patent Application No. 2019-139397, filed Jul. 30, 2019, the entire disclosure of which is incorporated by reference herein.

BACKGROUND

The present disclosure relates to an ophthalmologic apparatus and ophthalmologic system used for measurement and imaging of a subject's eye.

Ophthalmologic apparatuses include, for example, an ophthalmologic measurement apparatus for measuring the characteristics of a subject's eye, and an ophthalmologic imaging apparatus for capturing an image of the subject's eye. In order to measure, or capture an image of, the subject's eye, the positions of the subject's eye (subject) and the ophthalmologic apparatus need to be adjusted. Therefore, ophthalmologic apparatuses that can move relative to the subject's eye has been proposed.

Japanese Unexamined Patent Publication No. 2018-51337 discloses an ophthalmologic apparatus having an apparatus body provided for a base unit via a driving unit. The apparatus body described in Japanese Unexamined Patent Publication No. 2018-51337 is provided with an intraocular pressure measurement unit that measures an intraocular pressure of the subject's eye, and an ocular characteristic measurement unit that measures other optical characteristics (ocular characteristics) of the subject's eye.

The driving unit described in Japanese Unexamined Patent Publication No. 2018-51337 moves the apparatus body with respect to the base unit in an up-down direction (Y-axis direction), a front-rear direction (Z-axis direction), and a left-right direction (X-axis direction) orthogonal to these directions. Specifically, the driving unit described in Japanese Unexamined Patent Publication No. 2018-51337 includes a Y-axis driving portion, a Z-axis driving portion, and an X-axis driving portion, and functions as a slide mechanism that slides the apparatus body in the up-down direction (Y-axis direction), the front-rear direction (Z-axis direction), and the left-right direction (X-axis direction) with respect to the base unit.

SUMMARY

However, if the apparatus is provided with a slide mechanism that slides the apparatus body having an examination unit including a measurement unit and an imaging unit, the driving unit becomes large in size, which makes the downsizing of the ophthalmologic apparatus difficult. Further, if this mechanism is used to give the apparatus body a wider movable range and a higher degree of freedom, the driving unit disadvantageously becomes much larger in size. If another mechanism for freely changing the orientation and inclination of the examination unit is provided, the driving unit becomes much larger in size.

The present disclosure has been made to solve the above-described problem, and it is therefore an object of the present disclosure to provide an ophthalmologic apparatus and an ophthalmologic system that are downsized, and give a measurement unit an increased degree of positioning freedom.

In order to achieve the above-described object, an ophthalmologic apparatus of the present disclosure is an ophthalmologic apparatus for optically acquiring information of a subject's eye. The ophthalmologic apparatus includes: a head unit having an optical system capable of receiving light reflected from the subject's eye; a drive mechanism that movably holds the head unit; an alignment detection unit that detects a position of the subject's eye relative to the head unit; and a control unit that controls the drive mechanism. The drive mechanism includes at least two arms rotatably connected together, at least two first rotation support mechanisms each of which is rotatable about a first axis, at least three second rotation support mechanisms each of which is rotatable about a second axis different in direction from the first axis, and at least five driving units for driving the first and second rotation support mechanisms, the first and second rotation support mechanisms allowing the head unit to move. The control unit is capable of controlling the driving units using a detection result of the alignment detection unit to align the head unit and the subject's eye with each other.

Further, in order to achieve the above-described object, an ophthalmologic system of the present disclosure is an ophthalmologic system for optically acquiring information of a subject's eye. The ophthalmologic system includes: a head unit having an optical system capable of receiving light reflected from the subject's eye; a drive mechanism that movably holds the head unit; an alignment detection unit that detects a position of the subject's eye relative to the head unit; a control unit that controls the drive mechanism; and a terminal device that receives information about the light received by the optical system via a network. The drive mechanism includes at least two arms rotatably connected together, at least two first rotation support mechanisms each of which is rotatable about a first axis, at least three second rotation support mechanisms each of which is rotatable about a second axis different in direction from the first axis, and at least five driving units for driving the first and second rotation support mechanisms, the first and second rotation support mechanisms allowing the head unit to move. The control unit is capable of controlling the driving units using a detection result of the alignment detection unit to align the head unit and the subject's eye with each other.

The present disclosure offering the above-described solution can provide an ophthalmologic apparatus and an ophthalmologic system which are downsized, and give a measurement unit an increased degree of positioning freedom.

DETAILED DESCRIPTION

Embodiments of the present disclosure will be described in detail with reference to the drawings.

First Embodiment

A first embodiment of the present disclosure will be described below.

Figure 1:
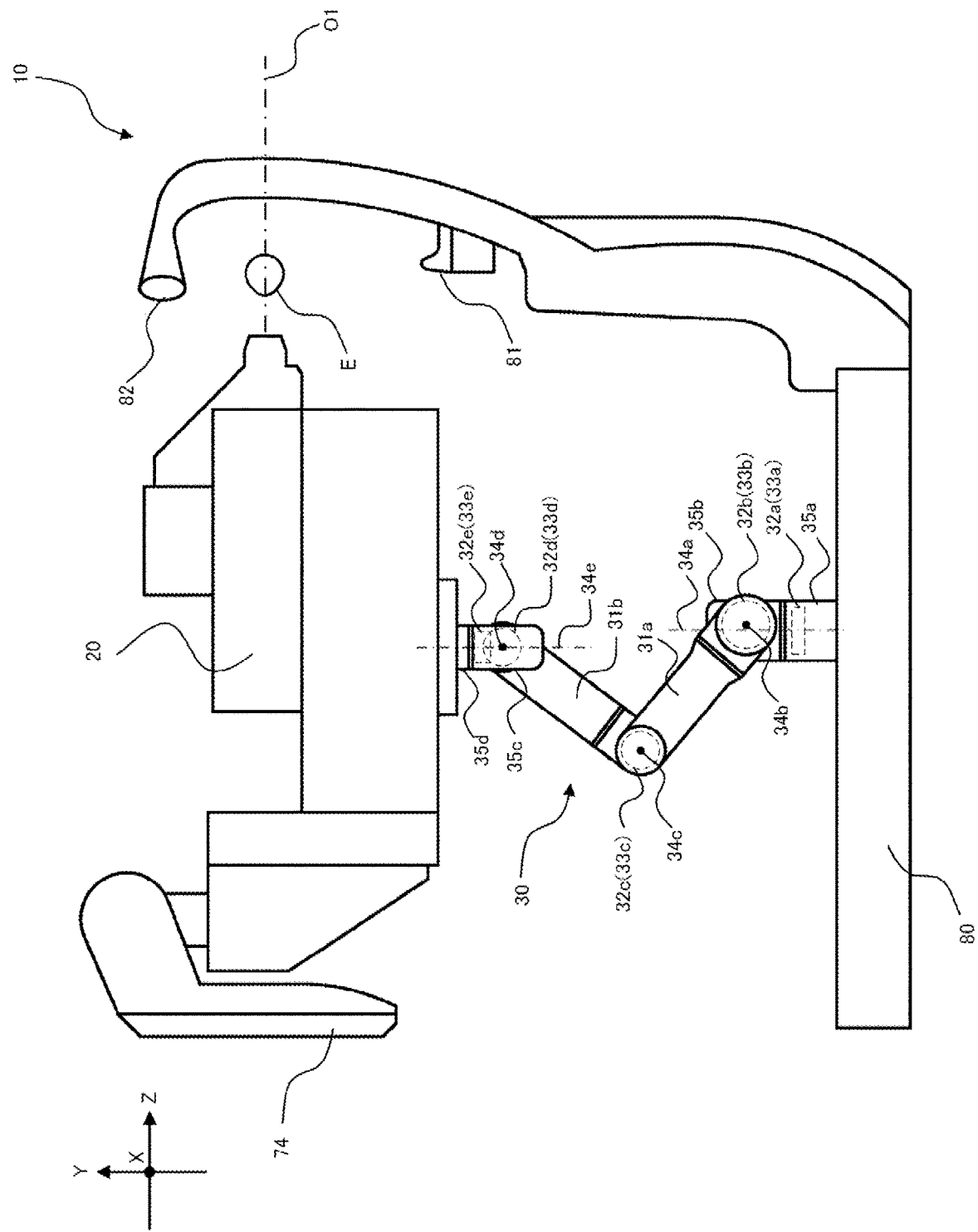
FIG. 1 is a schematic view illustrating a configuration of an ophthalmologic apparatus according to a first embodiment of the present disclosure.

FIG. 1 is a side view illustrating an ophthalmologic apparatus of the first embodiment. An ophthalmologic apparatus 10 of the present embodiment irradiates a subject's eye E with light, and acquires information about the characteristics of the subject's eye based on the detection result of light reflected from the subject's eye E. Specifically, the ophthalmologic apparatus 10 of the present embodiment is an ophthalmologic apparatus that examines the subject's eye E based on the light reflected from the subject's eye E. The examination by the ophthalmologic apparatus generally includes measurement for acquiring the characteristics of the subject's eye E, and photographing for capturing an image of the subject's eye E.

Examples of an ophthalmologic measurement apparatus include: an eye refraction test apparatus (a refractometer, a keratometer) that measures refractive characteristics of the subject's eye; a tonometer; a specular microscope that acquires corneal characteristics (e.g., thickness and cellular distribution of cornea); a wavefront analyzer that acquires aberration information of the subject's eye using a Hartmann-Shack sensor; and an eye axis length measurement apparatus. More specifically, the refractometer measures eye refraction by irradiating a posterior segment with a ring image, and analyzing a reflected image of the posterior segment captured by the camera. The keratometer measures the eye refraction by irradiating an anterior segment with a ring image, and analyzing a reflected image captured by an anterior segment Examples of an ophthalmologic imaging apparatus include: an optical coherence tomography that acquires a cross-sectional image using optical coherence tomography (OCT); a fundus camera that captures a fundus image; a scanning laser ophthalmoscope (SLO) that captures a fundus image through laser scanning using a confocal optical system; and a slit lamp that uses slit light and cuts an optical section of the cornea to obtain an image.

Figure 2:
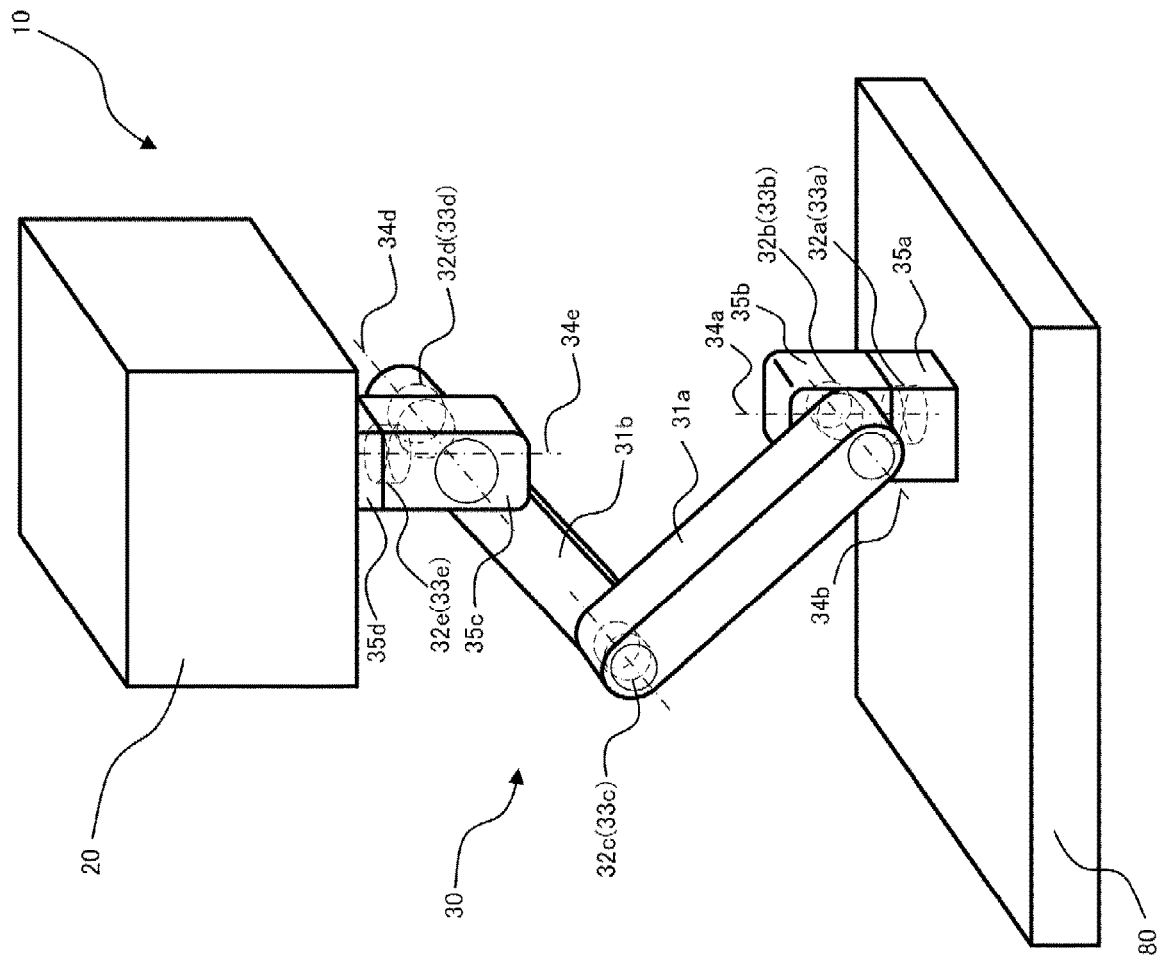
FIG. 2 is a perspective view illustrating the ophthalmologic apparatus according to the first embodiment of the present disclosure.
Figure 2:
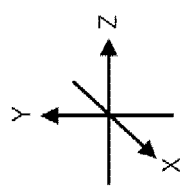
Figure 3:
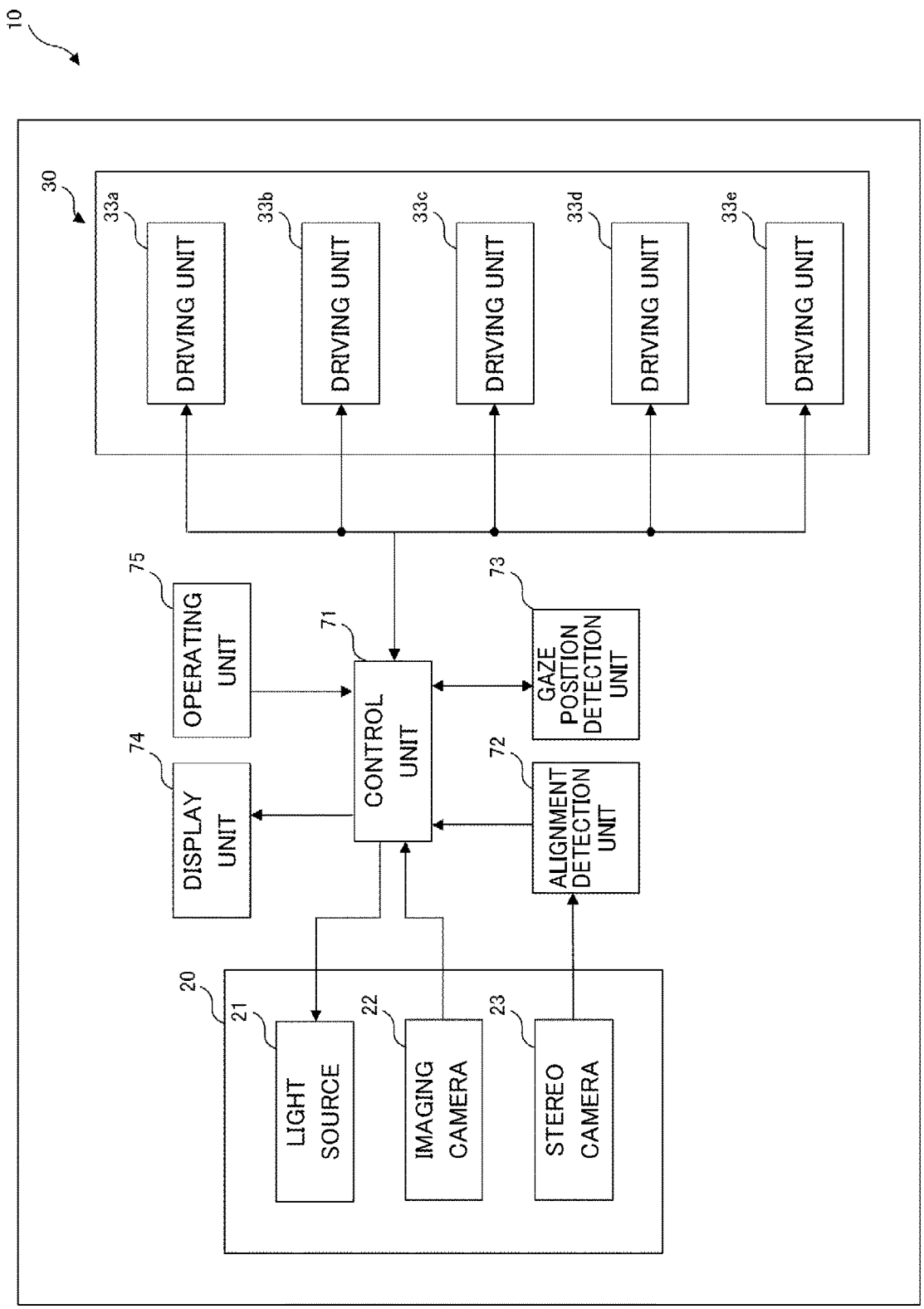
FIG. 3 is a block diagram illustrating the ophthalmologic apparatus according to the first embodiment of the present disclosure.

FIG. 1 is a schematic view illustrating the ophthalmologic apparatus 10 of the first embodiment. FIG. 2 is a perspective view illustrating a drive mechanism 30 of the ophthalmologic apparatus 10 of the first embodiment. FIG. 3 is a block diagram illustrating connection among components of the ophthalmologic apparatus 10 of the first embodiment. The configuration of the ophthalmologic apparatus 10 of the first embodiment will be described below with reference to FIGS. 1, 2, and 3.

The ophthalmologic apparatus 10 of the first embodiment includes a head unit 20, a drive mechanism 30, a display unit 74, a base unit 80, a chin support 81, and a forehead support 82. The head unit 20 is provided for the base unit 80 via the drive mechanism 30.

The head unit 20 includes an intraocular pressure measurement unit (not shown), and an ocular characteristic measurement unit (not shown). That is, the ophthalmologic apparatus 10 of the present embodiment is a hybrid ophthalmologic apparatus including the intraocular pressure measurement unit and the ocular characteristic measurement unit. The intraocular pressure measurement unit measures the intraocular pressure of the subject's eye. The ocular characteristic measurement unit measures other optical characteristics (ocular characteristics) of the subject's eye. However, at least any one of a measurement unit or an imaging unit provided in the head unit 20 is not limited to the intraocular pressure measurement unit and the ocular characteristic measurement unit. For example, the ophthalmologic apparatus 10 may be a hybrid ophthalmologic apparatus including an optical coherence tomography that acquires a cross-sectional image using OCT, and a fundus camera that captures a fundus image. Specifically, the ophthalmologic apparatus 10 of the present embodiment may be comprised of either one of the ophthalmologic imaging apparatus or the ophthalmic measurement apparatus described by way of examples listed above, or a plurality of the ophthalmologic measurement apparatuses or the ophthalmologic measurement apparatuses in combination. As described above, the head unit 20 includes an examination unit including at least one of an imaging unit having an imaging function or a measurement unit having a measurement function. In the present embodiment, it will be described as an example in which the head unit 20 includes, as the examination unit, the intraocular pressure measurement unit and the ocular characteristic measurement unit.

Each of the intraocular pressure measurement unit and the ocular characteristic measurement unit provided for the head unit 20 has an examination optical system for optically examining the subject's eye E. For example, each of the intraocular pressure measurement unit and the ocular characteristic measurement unit includes, as the examination optical system, an illumination optical system including a light source 21 that irradiates the anterior segment and fundus of the subject's eye E with illumination light, an imaging optical system including an imaging camera 22 (e.g., an anterior segment camera and a fundus camera) for acquiring images of the anterior segment and fundus of the subject's eye E. The subject's eye E is irradiated with the light emitted from the light source 21 of the examination optical system as a light beam parallel to an optical axis O1 of the examination optical system. The head unit 20 also includes a stereo camera 23 for alignment adjustment so that an appropriate distance is kept between the subject's eye E and the head unit 20. The stereo camera 23 includes at least two alignment cameras. An alignment detection unit 72, which will be described later, can detect the position of the subject's eye E relative to the head unit 20 from the information of images captured by the two alignment cameras.

The display unit 74 is comprised of a liquid crystal display, and displays an image such as an anterior segment image, and examination results of the subject's eye E under the control of the control unit 71. In the present embodiment, the display unit 74 has a touch panel function to serve as an operating unit 75, which can be operated by a user to perform measurement using the intraocular pressure measurement unit or the ocular characteristic measurement unit, and to move the head unit 20. If the user points at the image of the subject's eye E on the touch panel of the display unit 74, the head unit 20 can be moved so that the pointed position comes to the center of the panel, or can be automatically moved through the alignment adjustment to adjust the focus. The head unit 20 may be manually moved through the operation via the operating unit 75. A measurement switch may be provided so that the measurement is performed via the operation of the measurement switch. Further, a control lever or a movement operation switch may be provided so that the head unit 20 is moved via the operation of the control lever or the movement operation switch.

The chin support 81 and the forehead support 82 fix the face of the subject with respect to the heat unit 20 during the measurement, so that the position of the subject's eye E is fixed with respect to the ophthalmologic apparatus 10. The chin support 81 is a portion on which the subject places his/her chin, and the forehead support 82 is a portion with which the forehead of the subject makes contact. The head unit 20 can be moved by the drive mechanism 30 with respect to the base unit 80. Thus, the head unit 20 is configured to be movable with respect to the subject's face fixed by the chin support 81 and the forehead support 82, i.e., the subject's eye E.

In the present specification, the gravity direction is defined as a Y direction which is a vertical direction, and directions perpendicular to the gravity direction and orthogonal to each other are defined as an X direction and a Z direction. Further, a direction along a plane defined by the X and Z directions is defined as a horizontal direction. A left-right direction in FIG. 1 will be regarded as the Z direction (the direction of the optical axis O1 of the examination optical system).

The drive mechanism 30 can move the head unit 20 in the vertical direction and the horizontal direction with respect to the base unit 80. In addition, the head unit 20 can be inclined in an arbitrary direction with respect to the vertical direction or the horizontal direction.

The drive mechanism 30 includes two arms 31a and 31b, five rotation support mechanisms 32a, 32b, 32c, 32d, and 32e, five driving units 33a, 33b, 33c, 33d, and 33e that respectively drive the rotation support mechanisms, and supports 35a, 35b, 35c, and 35d. Each of the rotation support mechanisms 32a, 32b, 32c, 32d, and 32e is provided for the arm or the support, and allows the counterpart arm or support connected thereto to rotate about an axis 34a, 34b, 34c, 34d, or 34e. Specifically, each of the rotation support mechanisms is a mechanism that rotatably holds a shaft body connecting two members (the arms, the supports, or the arm and the support). The driving units 33a, 33b, 33c, 33d, and 33e are, for example, motors each of which generates a driving force for rotating an associated one of the rotation support mechanisms 32a, 32b, 32c, 32d, and 32e. Specifically, each driving unit is, for example, a mechanism including a combination of a DC motor and an encoder, and can be controlled at a predetermined rotation angle. Each driving unit may be a stepping motor. Further, the motor may be integrated with a speed reducer. In the present specification, the driving unit and an associated one of the rotation support mechanisms are illustrated as an integrated part. For example, the rotation support mechanism 32a and the driving unit 33a for driving the rotation support mechanism unit 32a are indicated by the reference character "32a(33a)." Note that the rotation support mechanism and the driving unit may be configured as separate parts. For example, the rotation support mechanism may be a mechanism that holds the shaft body using a bearing, and the driving unit may be configured to transmit a rotational driving force to a geared shaft body held by the bearing via a reduction gear.

The configuration of the drive mechanism 30 will be described in more detail below. The arm 31a is connected to the base unit 80 via the support 35b and the support 35a fixed to the base unit 80. More specifically, the support 35b is connected to the support 35a fixed to the base unit 80 to be rotatable about the axis 34a by the rotation support mechanism 32a (corresponding to a first rotation support mechanism) provided for the support 35a. Further, the arm 31a is connected to the support 35b to be rotatable about the axis 34b by the rotation support mechanism 32b (corresponding to a second rotation support mechanism) provided for the support 35b. The arm 31b is connected to the arm 31a to be rotatable by the rotation support mechanism 32c (corresponding to the second rotation support mechanism) provided for the arm 31a. The arm 31b and the head unit 20 are connected together via the supports 35c and 35d. More specifically, the support 35c is connected to the arm 31b to be rotatable about the axis 34d via the rotation support mechanism 32d (corresponding to the second rotation support mechanism) provided for the arm 31b. The support 35d is connected to the support 35c to be rotatable about the axis 34e via the rotation support mechanism 32e (corresponding to the first rotation support mechanism) provided for the support 35c. Each of the rotation support mechanisms may be provided for a member to be connected.

In FIGS. 1 and 2, the axes 34a and 34e are axes that can be oriented in the Y direction, i.e., the vertical direction, and these two axes 34a and 34e correspond to an example of a first axis of the present disclosure. The axes 34b, 34c, and 34d are axes that can be oriented in the X direction, i.e., the horizontal direction, and these three axes 34b, 34c, and 34d correspond to an example of a second axis of the present disclosure. Note that the axes are not necessarily in the above-described relationship in the process in which the drive mechanism 30 is operated.

FIG. 3 is a block diagram illustrating electrical connection among components of the ophthalmologic apparatus 10 of the first embodiment. A control unit 71 is a controller incorporated in the base unit 80. The control unit 71 can instruct the light source 21 to irradiate the subject's eye E with light. The control unit 71 can also receive information from the imaging camera 22, analyze the received captured image data, and display the captured image data and the analysis result on the q 74. The alignment detection unit 72 can calculate information about the position of the subject's eye relative to the head unit based on the information from the stereo camera 23. Based on the information about the relative position calculated by the alignment detection unit 72, the control unit 71 can control some of the driving units 33a, 33b, 33c, 33d, and 33e as needed to move the head unit 20 so that the head unit 20 and the subject's eye E have an appropriate positional relationship.

A gaze position detection unit 73 has the function of receiving the captured image data input from the imaging camera 22 via the control unit 71, detecting a gaze position of the subject's eye E, calculating a gaze direction from the detected gaze position, and transmitting the calculated gaze direction to the control unit 71. The gaze position detection unit 73 can detect the gaze position of the subject's eye E by, for example, a gaze direction detection method (corneal detection method) using a Purkinje image. The near-infrared light enters the subject's eye E from the light source 21. The near-infrared light incident from the point light source generates a Purkinje image, which is the reflection of the near-infrared light, on a surface of a cornea Ea of the subject's eye E. The position of the Purkinje image changes in accordance with the change in the gaze direction of the subject's eye E. Thus, the gaze position detection unit 73 can detect position coordinates C1 of the Purkinje image on the subject's eye E based on the captured image data of the subject's eye E entered from the imaging camera 22. Then, the gaze position detection unit 73 can detect the gaze direction of the subject's eye E based on the position (gaze position) of the center of a pupil relative to the position of the Purkinje image indicated by the position coordinates C1. Note that the gaze direction may be detected by any other method.

The gaze position detecting unit 73 detects the position of the subject's eye E relative to the imaging camera 22 based on the captured image data. Note that the method for detecting the relative position of the subject's eye E is not particularly limited. In this case, the gaze position detection unit 73 functions as a subject's eye position detection unit that detects the position of the subject's eye E relative to the head unit 20.

Next, how the ophthalmologic apparatus 10, in particular, the drive mechanism 30, is operated will be described. The control unit 71 controls the driving unit 33a to allow the support 35b and the arm 31a connected thereto to rotate about the axis 34a, and allow the head unit 20 to change its orientation (inclination) in an XZ plane. The control unit 71 controls the driving unit 33b to allow the arm 31a to rotate about the axis 34b, and allow the head unit 20 to change its position in the X, Y, and Z directions, or its inclination (orientation). The control unit 71 controls the driving unit 33c to allow the arm 31b to rotate about the axis 34c, and allow the head unit 20 to change its position in the X, Y, and Z directions, or its inclination (orientation). The control unit 71 controls the driving unit 33d to allow the support 35c to rotate about the axis 34d, and allow the head unit 20 to change its inclination (orientation). Further, the control unit 71 controls the driving unit 33e to allow the support 35d to rotate about the axis 34e, and allow the head unit 20 to change its orientation (inclination).

Controlling the driving units 33a, 33b, 33c, 33d, and 33e in this manner, the control unit 71 allows the head unit 20 to move to an arbitrary position in an XYZ space, and to incline in an arbitrary direction or change its orientation. Based on the gaze position of the subject's eye E detected by the gaze position detection unit 73 (detection result), the control unit 71 can control the driving units 33a, 33b, 33c, 33d, and 33e to orient the head unit 20 so that the optical axis O1 of the examination optical system and the gaze direction substantially coincide with each other. Further, the control unit 71 may control the driving units 33a, 33b, 33c, 33d, and 33e to orient the head unit 20 so that the optical axis O1 of the examination optical system deviates from the gaze direction with respect to the gaze direction. For example, when obtaining a cross-sectional image of an eye E of a subject having a cataract through capturing a fundus image or OCT, the head unit 20 is oriented so that the optical axis O1 of the examination optical system avoids a cloudy portion of the lens of the subject's eye E. This makes it possible to examine the eye of the subject having a cataract. In this way, the head unit 20 can be arbitrarily positioned or oriented with respect to the subject's eye E, which makes it possible to examine the subject's eye E at an arbitrary position, or in an arbitrary direction.

Further, if the driving units are controlled in synchronization, the position of the head unit 20 can be changed while maintaining the inclination and orientation of the head unit 20. This can move the head unit 20 with its posture maintained, so that the optical axis O1 of the examination optical system is aligned with a direction toward the subject's eye E.

Further, if the driving units are controlled in synchronization, the inclination and orientation of the head unit 20 can be changed while allowing the optical axis O1 of the examination optical system to pass an eye rotation center, which is the center of rotation of the subject's eye E, or its vicinity (substantial eye rotation center).

The alignment detection unit 72 can calculate the information about the position of the subject's eye E relative to the head unit 20 based on the information from the stereo camera 23. For example, determining that the position of the subject's eye E relative to the head unit 20 is far from an appropriate position, i.e., they have a great distance in the X direction, the control unit 71 drives the driving units 33d, 33c, and 33b in synchronization to cause the head unit 20 to move to the right, which is the Z direction in FIG. 1, while maintaining the posture, and the position in the Y direction, of the head unit 20. The control unit 71 may control the drive mechanism 30 in accordance with the distance information from the alignment detection unit 72 to move the head unit 20, or may perform feedback control using the information about the relative position sequentially output from the alignment detection unit 72 to move the head unit 20.

Further, the control unit 71 may control the respective driving units in accordance with an operation through the operating unit 75 to move the head unit 20.

As can be seen in the foregoing, according to the ophthalmologic apparatus 10 of the embodiment of the present disclosure, the ophthalmologic apparatus 10 which is downsized, and gives the head unit 20 an increased degree of positioning freedom can be provided without using a slide mechanism. Further, the structure can be simplified while improving the degree of positioning freedom of the head unit 20. Controlling the drive mechanism 30 in accordance with the information from the alignment detection unit 72, the control unit 71 can cause the head unit 20 and the subject's eye E to be automatically aligned with each other to be in an appropriate positional relationship.

Variation of First Embodiment

Figure 4:
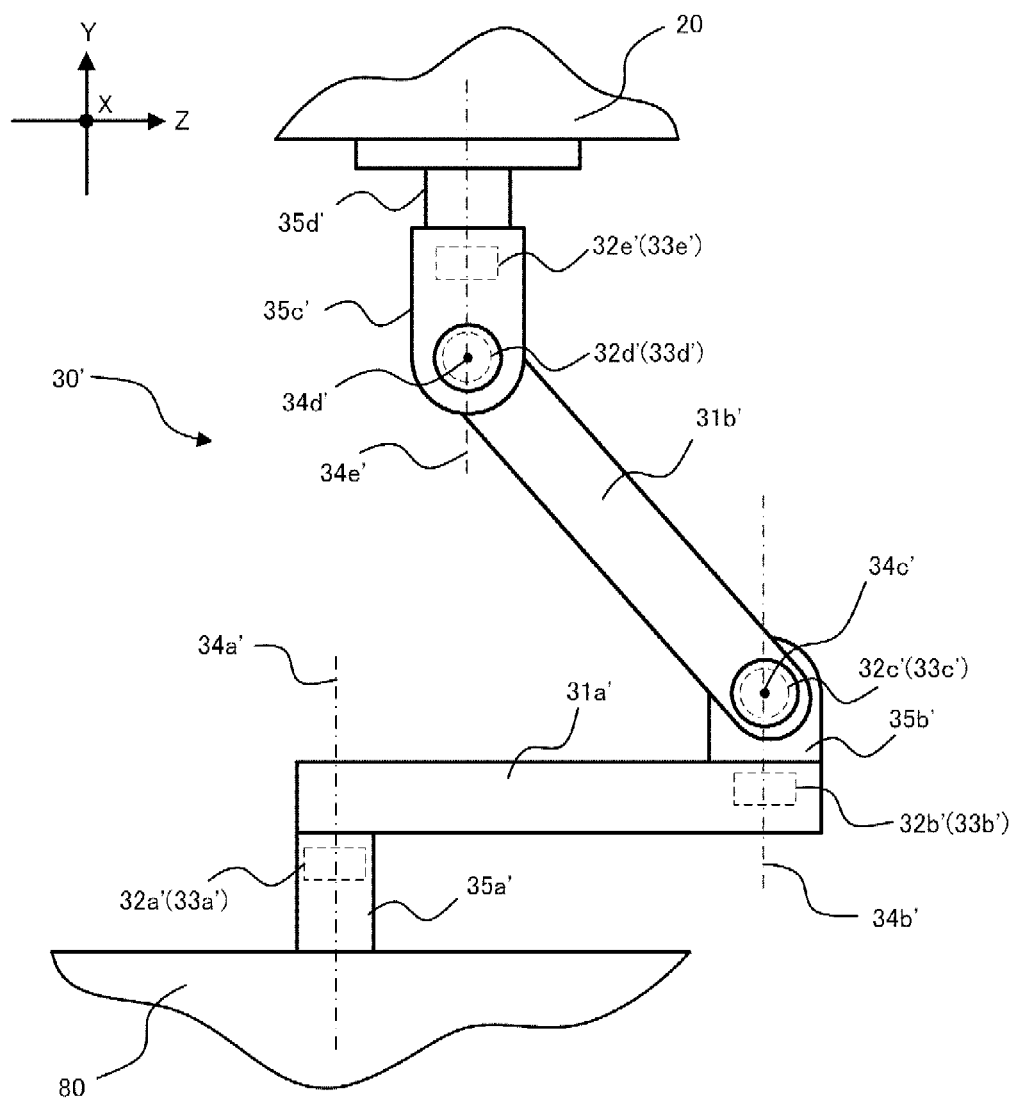
FIG. 4 is a schematic view illustrating a variation of a drive mechanism of the ophthalmologic apparatus according to the first embodiment of the present disclosure.

A variation of the ophthalmologic apparatus 10 according to the first embodiment will be described below. In this variation, unlike the first embodiment, one of the arms can rotate and move only in the horizontal direction. FIG. 4 is a schematic view illustrating, in an enlarged scale, a drive mechanism 30' of the ophthalmologic apparatus 10 as a variation of the drive mechanism of the ophthalmologic apparatus according to the first embodiment.

The drive mechanism 30' includes two arms 31a' and 31b', five rotation support mechanisms 32a', 32b', 32c', 32d', and 32e', five driving units 33a', 33b', 33c', 33d', and 33e' that respectively drive the rotation support mechanisms, and supports 35a', 35b', 35c', and 35d'. Each of the rotation support mechanisms 32a', 32b', 32c', 32d', and 32e' is provided for the arm or the support, and allows the counterpart arm or support connected thereto to rotate about an axis 34a', 34b', 34c', 34d', or 34e'.

The configuration of the drive mechanism 30' will be described in more detail below. The arm 31a' is connected to the base unit 80 to be rotatable about the axis 34a' by the support 35a' fixed to the base unit 80 and the rotation support mechanism 32a' (corresponding to a second rotation support mechanism) provided for the support 35a'. This allows the arm 31a' to rotate and move in the horizontal direction. The arm 31b' is connected to the arm 31a' via the support 35b'. More specifically, the support 35b' is connected to the arm 31a' to be rotatable about the axis 34b' via the rotation support mechanism 32b' (corresponding to the second rotation support mechanism) provided for the arm 31a'. The arm 31b' is connected to the support 35b' to be rotatable about the axis 34c' via the rotation support mechanism portion 32c' (corresponding to a first rotation support mechanism) provided for the support 35b'. The arm 31b' and the head unit 20 are connected together via the supports 35c' and 35d'. More specifically, the support 35c' is connected to the arm 31b' to be rotatable about the axis 34d' via the rotation support mechanism 32d' (corresponding to the first rotation support mechanism) provided for the arm 31b'. The support 35d' is connected to the support 35c' to be rotatable about the axis 34e' via the rotation support mechanism 32e' (corresponding to the second rotation support mechanism) provided for the support 35c'. Each of the rotation support mechanisms may be provided for a member to be connected.

In FIG. 4, the axes 34c' and 34d' are axes that can be oriented in the X direction, i.e., the horizontal direction, and the two axes 34c' and 34d' correspond to an example of a first axis of the present disclosure. The axes 34a', 34b', and 34e' are axes that can be oriented in the Y direction, i.e., the vertical direction, and the three axes 34a', 34b', and 34e' correspond to an example of a second axis of the present disclosure. Note that the axes are not necessarily in the above-described relationship in the process in which the drive mechanism 30' is operated.

Next, how the drive mechanism 30' is operated will be described below. The control unit 71 controls the driving unit 33a' to allow the arm 31a' to rotate about the axis 34a', and allow the head unit 20 to change its position in the X, Y, and Z directions, or its orientation (inclination). The control unit 71 controls the driving unit 33b' to allow the support 35b' to rotate about the axis 34b', and allow the head unit 20 to change its position in the X, Y, and Z directions, or its orientation (inclination). The control unit 71 controls the driving unit 33c' to allow the arm 31b' to rotate about the axis 34c', and allow the head unit 20 to change its position in the X, Y, and Z directions, or its inclination (orientation). The control unit 71 controls the driving unit 33d' to allow the support 35c' to rotate about the axis 34d', and allow the head unit 20 to change its inclination (orientation). The control unit 71 controls the driving unit 33e' to allow the support 35d' to rotate about the axis 34e', and allow the head unit 20 to change its orientation (inclination). Controlling the driving units 33a', 33b', 33c', 33d', and 33e' in this manner, the control unit 71 allows the head unit 20 to move to an arbitrary position in an XYZ space, and to incline in an arbitrary direction or change its orientation.

As can be seen in the foregoing, even if the drive mechanism is configured such that one of the arms is capable of rotating and moving only in the horizontal direction, and two of the five axes are oriented in the horizontal direction and the remaining three axes are oriented in the vertical direction, the head unit 20 is allowed to move to an arbitrary position in the XYZ space, and to incline in an arbitrary direction or change its orientation, in the same manner as in the first embodiment.

Another Variation of First Embodiment

Figure 5:
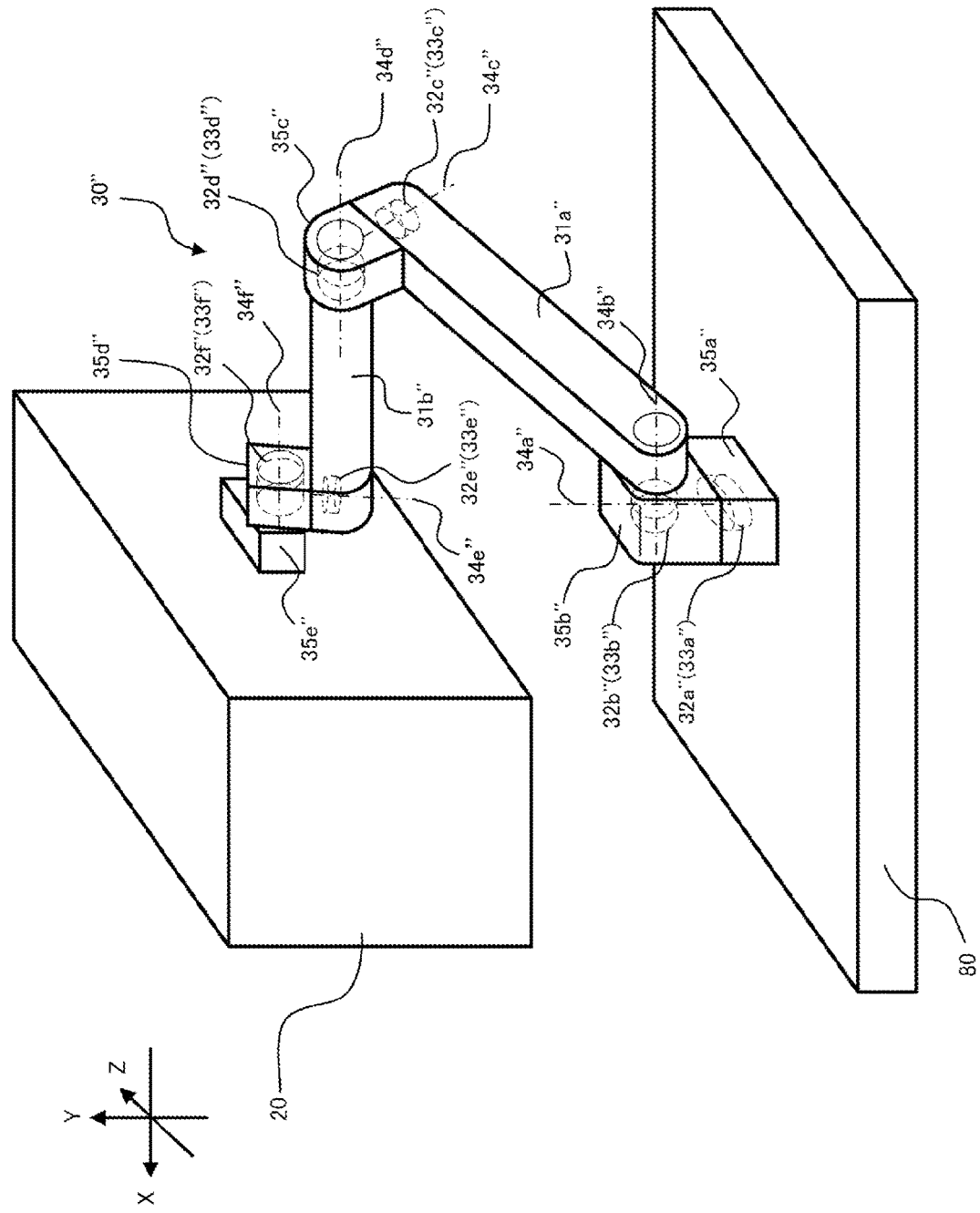
FIG. 5 is a perspective view illustrating another variation of the ophthalmologic apparatus according to the first embodiment of the present disclosure.

Another variation of the ophthalmologic apparatus 10 according to the first embodiment will be described below. In this variation, unlike the first embodiment, an additional rotation support mechanism is provided between the two arms. FIG. 5 is a schematic perspective view illustrating another variation of the drive mechanism of the ophthalmologic apparatus according to the first embodiment.

A drive mechanism 30" includes two arms 31a" and 31b", six rotation support mechanisms 32a", 32b", 32c", 32d", 32e", and 32f", six driving units 33a", 33b", 33c", 33d", 33e", and 33f" that respectively drive the rotation support mechanisms, and supports 35a", 35b", 35c", 35d", and 35e". Each of the rotation support mechanisms 32a", 32b", 32c", 32d", 32e", and 32f" is provided for the arm or the support, and allows the counterpart arm or support connected thereto to rotate about an axis 34a", 34b", 34c", 34d", 34e", or 34f".

The configuration of the drive mechanism 30" will be described in more detail below. The arm 31a" is connected to the base unit 80 via the support 35b" and the support 35a" fixed to the base unit 80. More specifically, the support 35b" is connected to the support 35a" fixed to the base unit 80 to be rotatable about the axis 34a" by the rotation support mechanism 32a" (corresponding to a first rotation support mechanism) provided for the support 35a". Further, the arm 31a" is connected to the support 35b" to be rotatable about the axis 34b" by the rotation support mechanism 32b" (corresponding to a second rotation support mechanism) provided for the support 35b". The arm 31b" is connected to the arm 31a" via the support 35c". More specifically, the support 35c" is connected to the arm 31a" to be rotatable about the axis 34c" via the rotation support mechanism 32c" (corresponding to the first rotation support mechanism) provided for the arm 31a". The arm 31b" is connected to the support 35c" to be rotatable about the axis 34d" via the rotation support mechanism portion 32d" (corresponding to the second rotation support mechanism) provided for the support 35c". The arm 31b" and the head unit 20 are connected together via the supports 35d" and 35e". More specifically, the support 35d" is connected to the arm 31b" to be rotatable about the axis 34e" via the rotation support mechanism 32e" (corresponding to the first rotation support mechanism) provided for the arm 31b". The support 35e" is connected to the support 35d" to be rotatable about the axis 34f" via the rotation support mechanism 32r (corresponding to the second rotation support mechanism) provided for the support 35d". Each of the rotation support mechanisms may be provided for a member to be connected.

In FIG. 5, the axes 34a", 34c", and 34e" are axes that can be oriented in the Y direction, i.e., the vertical direction, and the three axes 34a", 34c" and 34e" correspond to an example of a first axis of the present disclosure. The axes 34b", 34d", and 34f" are axes that can be oriented in the X direction, i.e., the horizontal direction, and the three axes 34b", 34d", and 34f" correspond to an example of a second axis of the present disclosure. Note that the axes are not necessarily in the above-described relationship in the process in which the drive mechanism 30" is operated.

Next, how the drive mechanism 30" is operated will be described below. The control unit 71 controls the driving unit 33a" to allow the support 35b" and the arm 31a" connected thereto to rotate about the axis 34a", and allow the head unit 20 to change its orientation (inclination) in an XZ plane. The control unit 71 controls the driving unit 33b" to allow the arm 31a" to rotate about the axis 34b", and allow the head unit 20 to change its position in the X, Y, and Z directions, or its inclination (orientation). The control unit 71 controls the driving unit 33c" to allow the support 35c" to rotate about the axis 34c", and allow the head unit 20 to change its position in the X, Y, and Z directions, or its inclination (orientation). The control unit 71 controls the driving unit 33d" to allow the arm 31b" to rotate about the axis 34d", and allow the head unit 20 to change its position in the X, Y, and Z directions, or its inclination (orientation). The control unit 71 controls the driving unit 33e" to allow the support 35d" to rotate about the axis 34e", and allow the head unit 20 to change its inclination (orientation). The control unit 71 controls the driving unit 33f" to allow the support 35e" to rotate about the axis 34f", and allow the head unit 20 to change its orientation (inclination).

As can be seen in the foregoing, using the drive mechanism including the three axes oriented in the horizontal direction and the remaining three axes oriented in the vertical direction, the control unit 71 controls the driving units 33a", 33b", 33c", 33d", 33e", and 33f" to allow the head unit 20 to move to an arbitrary position in the XYZ space, and to incline in an arbitrary direction or change its orientation. Having six rotation axes, the drive mechanism 30" can move the head unit 20 more smoothly than the drive mechanism having five rotation axes.

The drive mechanism 30 of the present embodiment is not limited to have two arms, and may have three or more arms. Further, the number of the rotation support mechanisms may be five or more, and the number of the driving units may be five or more.

Second Embodiment

A second embodiment of the present disclosure will be described below. An ophthalmologic apparatus 10A according to the second embodiment is an apparatus that can acquire information simultaneously from both eyes of the subject, and has two head units respectively provided for the subject's right and left eyes to conduct simultaneous examination of the eyes.

Figure 6:
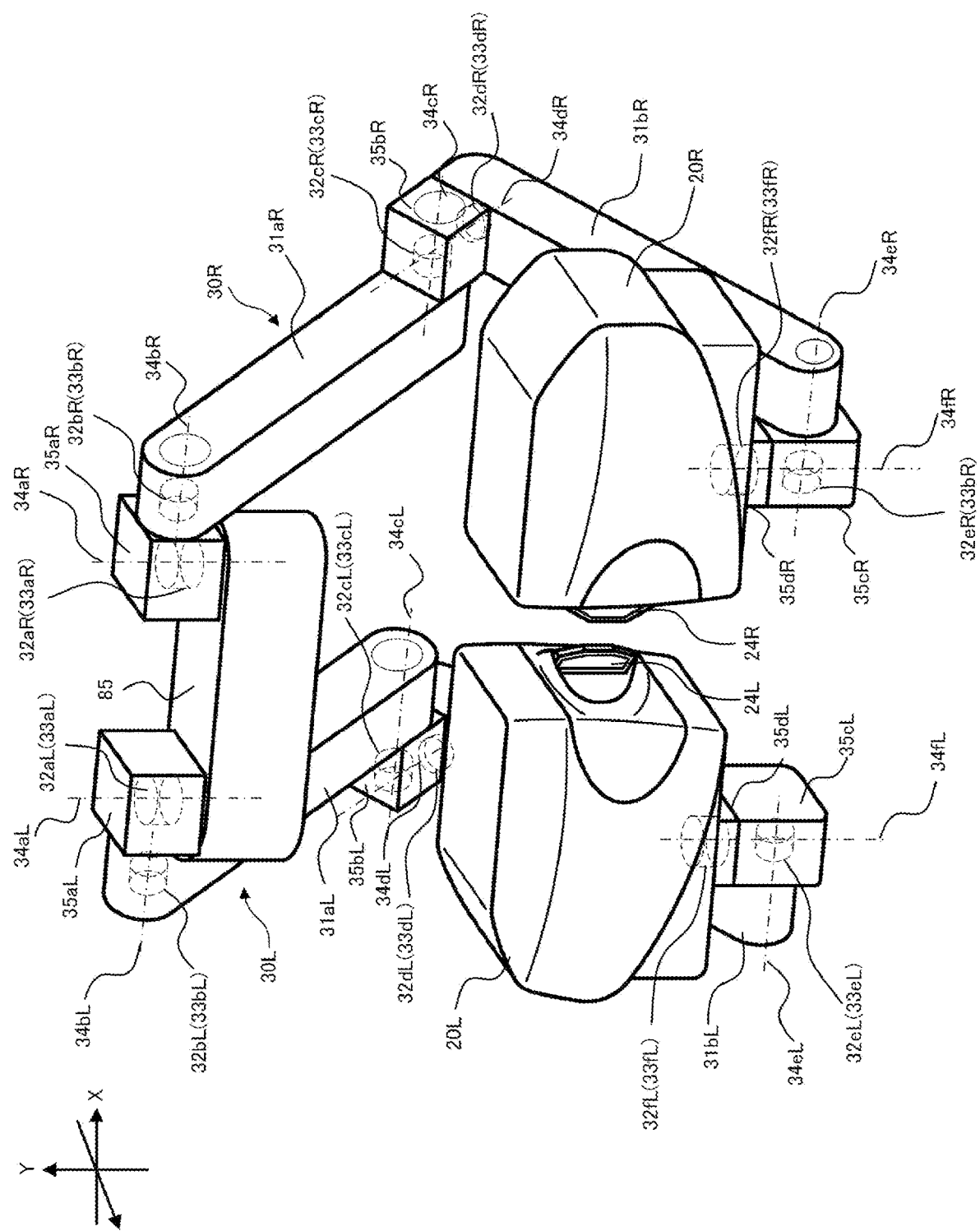
FIG. 6 is a perspective view partially illustrating an ophthalmologic apparatus according to a second embodiment of the present disclosure.
Figure 7:
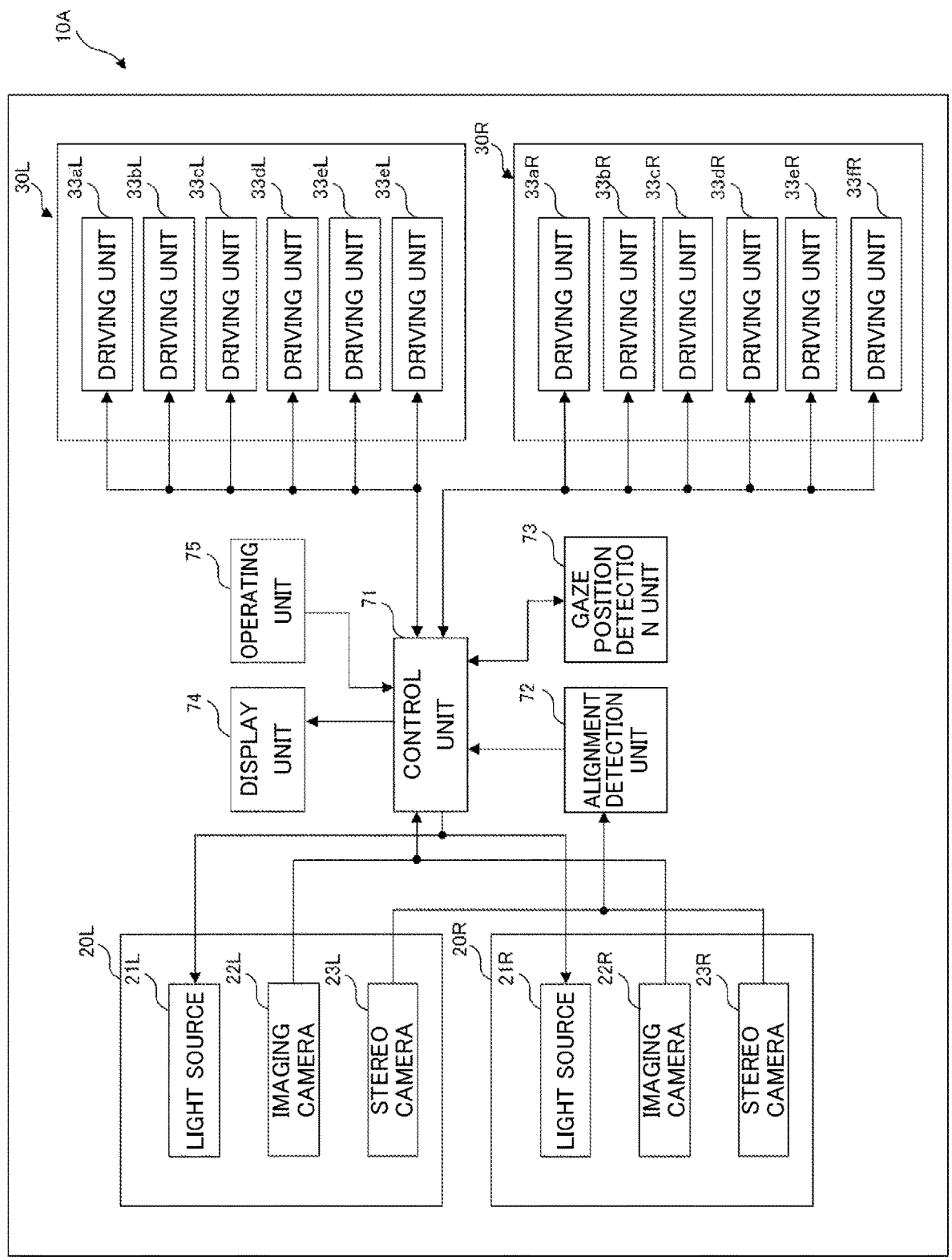
FIG. 7 is a block diagram illustrating the ophthalmologic apparatus according to the second embodiment of the present disclosure.

FIG. 6 is a perspective view illustrating head units and drive mechanisms of the ophthalmologic apparatus 10A of the second embodiment. FIG. 6 shows head units 20L and 20R, drive mechanisms 30L and 30R, and a frame unit 85 of the ophthalmologic apparatus 10A, but other components are not shown. Although not shown, the chin support and the forehead support described in the first embodiment may be provided for the ophthalmologic apparatus 10A to fix the face of the subject. FIG. 7 is a block diagram illustrating connection among components of the ophthalmologic apparatus 10A of the second embodiment. The configuration of the ophthalmologic apparatus 10A of the second embodiment will be described below with reference to FIGS. 6 and 7. The same reference characters are given to the same components as those of the first embodiment, and a description thereof is omitted. The subject's left eye will be denoted by reference character EL, and a cornea of the subject's eye EL by reference character EaL. Likewise, the subject's right eye will be denoted by reference character ER, and a cornea of the subject's eye ER by reference character EaR.

In FIG. 6, the left drive mechanism 30L and the right drive mechanism 30R are connected to the frame unit 85 fixed to a support column (not shown) supported by a base unit of the ophthalmologic apparatus 10A. The left head unit 20L is connected to the left drive mechanism 30L, and the right head unit 20R is connected to the right drive mechanism 30R. Specifically, the left head unit is paired with the left drive mechanism, and the right head unit is paired with the right drive mechanism. The two head units 20L and 20R are configured to be able to receive light reflected from the subject's right and left eyes EL and ER, respectively.

A drive mechanism 30L includes two arms 31aL and 31bL, six rotation support mechanisms 32aL, 32bL, 32cL, 32dL, 32eL, and 32fL, six driving units 33aL, 33bL, 33cL, 33dL, 33eL, and 33fL that respectively drive the rotation support mechanisms, and supports 35aL, 35bL, 35cL, and 35dL. Each of the rotation support mechanisms 32aL, 32bL, 32cL, 32dL, 32eL, and 32fL is provided for the arm or the support, and allows the counterpart arm or support connected thereto to rotate about an axis 34aL, 34bL, 34cL, 34dL, 34eL, or 34fL.

The configuration of the drive mechanism 30L will be described in more detail below. The arm 31aL is connected to the frame unit 85 via the support 35aL. More specifically, the support 35aL is connected to be rotatable about the axis 34aL by the rotation support mechanism 32aL (corresponding to a first rotation support mechanism) provided for the support 35aL. Further, the arm 31aL is connected to the support 35aL to be rotatable about the axis 34bL by the rotation support mechanism 32bL (corresponding to a second rotation support mechanism) provided for the arm 31aL. The arm 31bL is connected to the arm 31aL via the support 35bL. More specifically, the support 35bL is connected to the arm 31aL to be rotatable about the axis 34cL via the rotation support mechanism 32cL (corresponding to the second rotation support mechanism) provided for the support 35bL. The arm 31bL is connected to the support 35bL to be rotatable about the axis 34dL via the rotation support mechanism 32dL (corresponding to the first rotation support mechanism) provided for the arm 31bL. The arm 31bL and the head unit 20L are connected together via the supports 35cL and 35dL. More specifically, the support 35cL is connected to the arm 31bL to be rotatable about the axis 34eL via the rotation support mechanism 32eL (corresponding to the second rotation support mechanism) provided for the support 35cL. The support 35dL is connected to the support 35cL to be rotatable about the axis 34fL via the rotation support mechanism 32fL (corresponding to the first rotation support mechanism) provided for the support 35dL. The head unit 20L is connected to the support 35dL. Each of the rotation support mechanisms may be provided for a member to be connected.

In FIG. 6, the axes 34aL, 34dL, and 34fL are axes that can be oriented in the Y direction, i.e., the vertical direction, and the three axes 34aL, 34dL and 34fL correspond to an example of a first axis of the present disclosure. The axes 34bL, 34cL, and 34eL are axes that can be oriented in the X direction, i.e., the horizontal direction, and the three axes 34bL, 34cL and 34eL correspond to an example of a second axis of the present disclosure. Note that the axes are not necessarily in the above-described relationship in the process in which the drive mechanism 30L is operated.

The drive mechanism 30R and the drive mechanism 30L are symmetrical in shape. Components of the drive mechanism 30R have the same functions and reference characters as those of the drive mechanism 30L except that "R" in the reference characters replaces "L."

The left and right head units 20L and 20R are provided as a pair to individually correspond to the subject's left and right eyes. The left head unit 20L acquires information of the subject's left eye EL, and the right head unit 20R acquires information of the subject's right eye ER.

A mirror 24L, which is a deflection member, is provided for the left head unit 20L. The information of the corresponding subject's eye EL is acquired by the examination optical system through the mirror 24L. The left head unit 20L is provided with an examination optical system for acquiring ocular information of the subject's eye EL. The examination optical system includes an illumination optical system including a light source 21L that irradiates the anterior segment and fundus of the subject's eye EL with illumination light, an imaging optical system including an imaging camera 22L for acquiring images of the anterior segment and fundus of the subject's eye EL. The head unit 20L also includes a stereo camera 23L for alignment adjustment so that an appropriate distance is kept between the subject's eye EL and the head unit 20L.

Components of the right head unit 20R have the same functions and reference characters as those of the left head unit 20L except that the alphabet "R" in the reference characters replaces the alphabet "L."

FIG. 7 shows a block diagram modified from the block diagram of the first embodiment shown in FIG. 3 to correspond to the left and right head units 20L and 20R and the left and right drive mechanisms 30L and 30R.

Next, how the drive mechanism 30L is operated will be described below. The control unit 71 controls the driving unit 33aL to allow the support 35aL and the arm 31aL connected thereto to rotate about the axis 34aL, and allow the head unit 20L to change its orientation (inclination) in an XZ plane. The control unit 71 controls the driving unit 33bL to allow the arm 31aL to rotate about the axis 34bL, and allow the head unit 20L to change its position in the X, Y, and Z directions, or its inclination (orientation). The control unit 71 controls the driving unit 33cL to allow the support 35bL to rotate about the axis 34cL, and allow the head unit 20L to change its position in the X, Y, and Z directions, or its inclination (orientation). The control unit 71 controls the driving unit 33dL to allow the arm 31bL to rotate about the axis 34dL, and allow the head unit 20L to change its position in the X, Y, and Z directions, or its inclination (orientation). The control unit 71 controls the driving unit 33eL to allow the support 35cL to rotate about the axis 34eL, and allow the head unit 20L to change its inclination (orientation). The control unit 71 controls the driving unit 33fL to allow the support 35dL to rotate about the axis 34fL, and allow the head unit 20L to change its orientation (inclination). The drive mechanism 30R is operated in the same manner as the drive mechanism 30L except that the alphabet "R" in the reference characters replaces the alphabet "L."

Controlling the drive mechanisms 30L and 30R, i.e., the driving units 33aL, 33bL, 33cL, 33dL, 33eL, 33fL, 33aR, 33bR, 33cR, 33dR, 33eR, and 33fR, in this manner, the control unit 71 allows each of the head units 20L and 20R to move to an arbitrary position in an XYZ space, and to incline in an arbitrary direction or change its orientation. Thus, the head units 20L and 20R can be arbitrarily positioned or oriented with respect to the subject's eyes EL and ER, which makes it possible to examine the subject's eyes EL and ER at an arbitrary position, or in an arbitrary direction. Further, the control unit 71 can control the drive mechanisms 30L and 30R using the detection result of the alignment detection unit 72, so that the head units 20L and 20R are aligned with and the subject's eyes EL and ER, respectively.

The gaze position detection unit 73 has the function of receiving the captured image data of the subject's left and right eyes EL and ER entered from the imaging cameras 22L and 22R via the control unit 71, detecting the gaze positions of the subject's eyes EL and ER, calculating the gaze directions from the detected gaze positions, and transmitting the calculated gaze directions to the control unit 71.

Figure 8A:
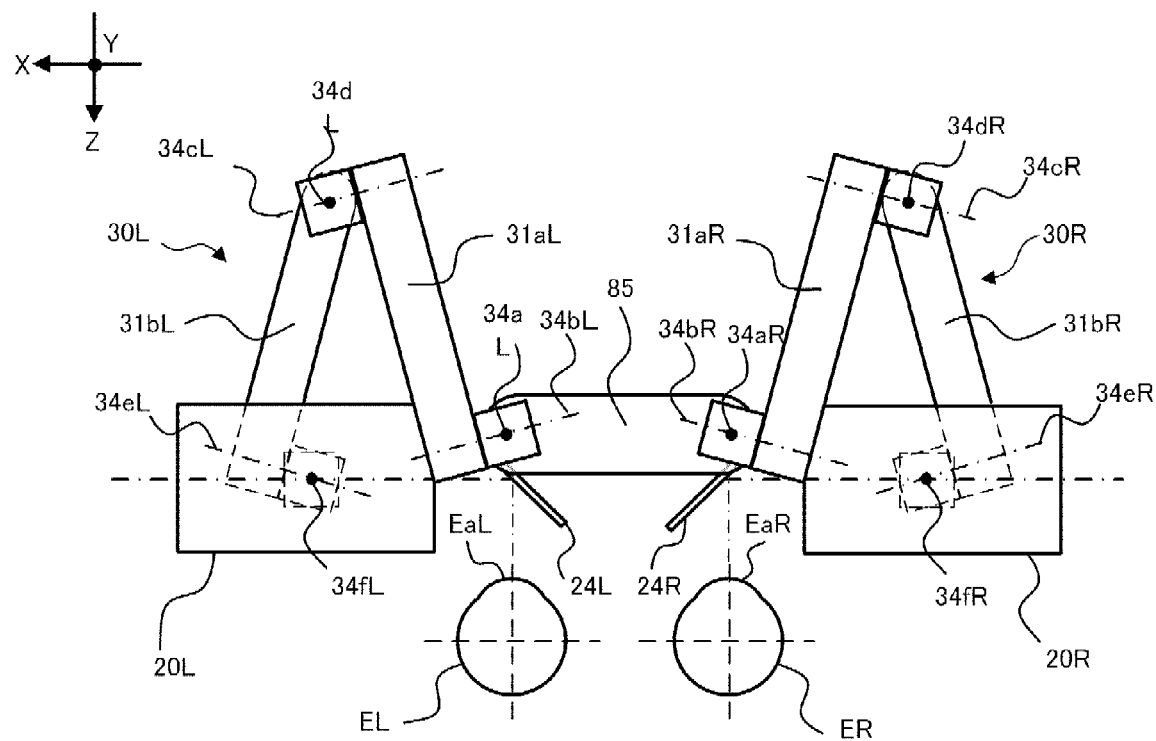
FIG. 8A is a schematic top view illustrating an operation of a head unit of the ophthalmologic apparatus according to the second embodiment of the present disclosure.
Figure 8B:
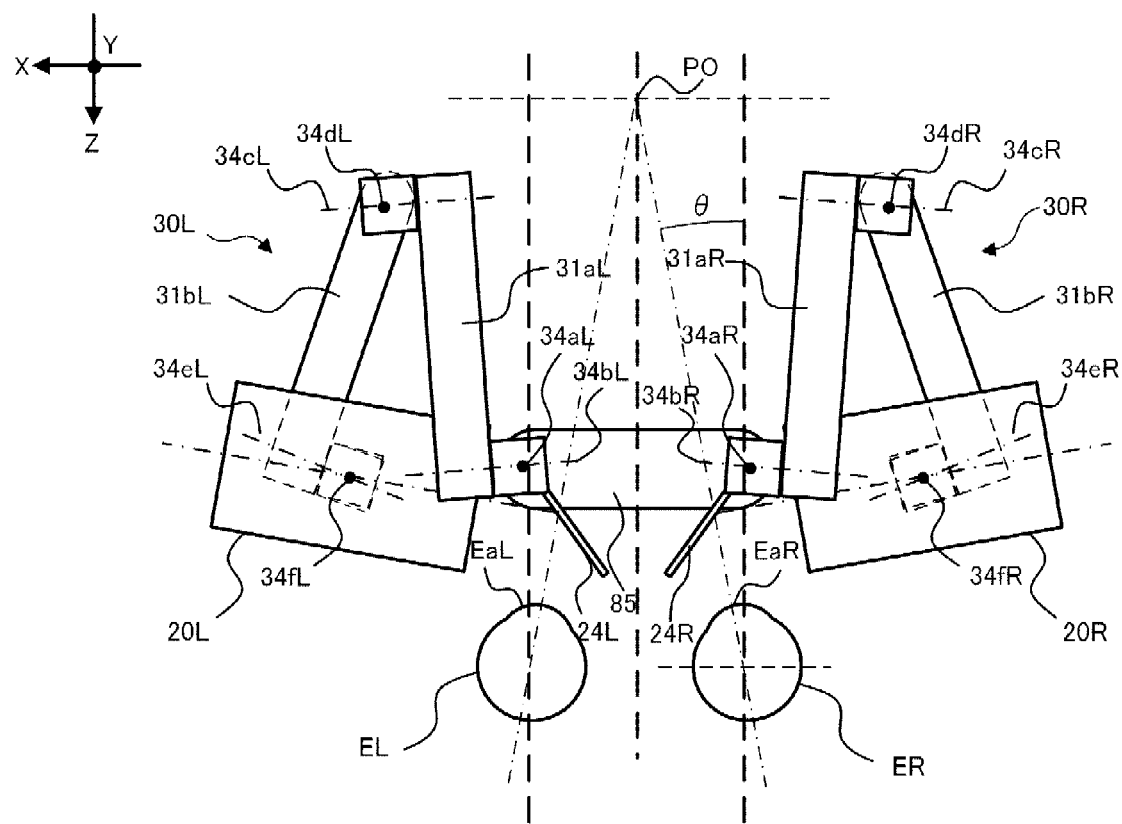
FIG. 8B is a schematic top view illustrating an operation of the head unit of the ophthalmologic apparatus according to the second embodiment of the present disclosure.

Next, referring to FIGS. 8A and 8B, it will be described how each of the head units 20L and 20R rotates in the direction of an XZ plane about the eye rotation center, which is the center of rotation, of an associated one of the subject's eyes EL and ER. FIGS. 8A and 8B are schematic views of the ophthalmologic apparatus 10A as viewed from the top.

FIG. 8A shows the subject's eyes EL and ER facing the front (the −Z direction). FIG. 8B shows the subject's eyes EL and ER in a near vision state. In order to bring the subject's eyes EL and ER into the near vision state, a fixation target (not shown) is used to guide the gaze of the subject's eyes EL and ER. Each of the subject's eye changes the gaze direction about the eye rotation center.

When the ophthalmologic apparatus 10A is used to perform, for example, a quantitative examination of squint in the near vision state, the control unit 71 controls the drive mechanisms 30L and 30R to allow the head units 20L and 20R to respectively rotate about the eye rotation centers of the subject's eyes EL and ER or the substantial eye rotation centers near the eye rotation centers, and the subject is instructed to fixate on the fixation target displayed at a fixation target point PO that is located forward by an examination distance from the subject's eyes E. This can bring the subject's eyes EL and ER into convergence, so that the eyes can gaze at the fixation target. If at least one of the subject's eyes EL and ER has a heterophoria and cannot be fixated on the target, the control unit 71 controls the drive mechanisms 30L and 30R to allow the head units to rotate so that an angle of convergence θ is aligned with the subject's eyes.

Figure 9A:
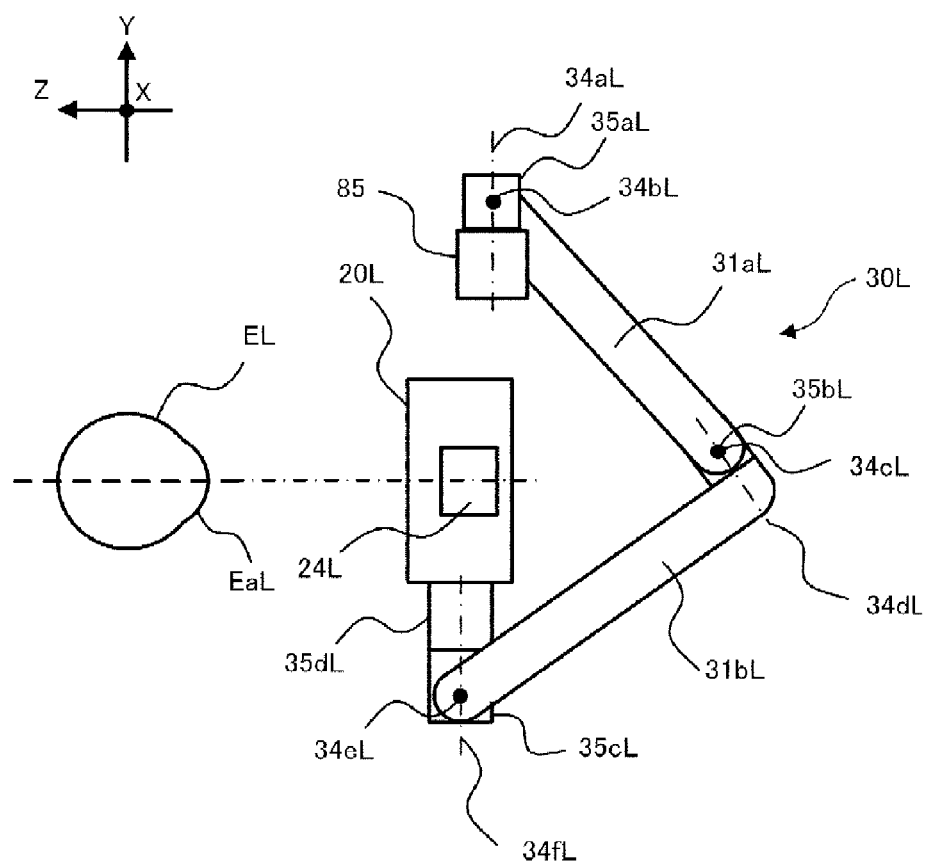
FIG. 9A is a schematic side view illustrating an operation of the head unit of the ophthalmologic apparatus according to the second embodiment of the present disclosure.
Figure 9B:
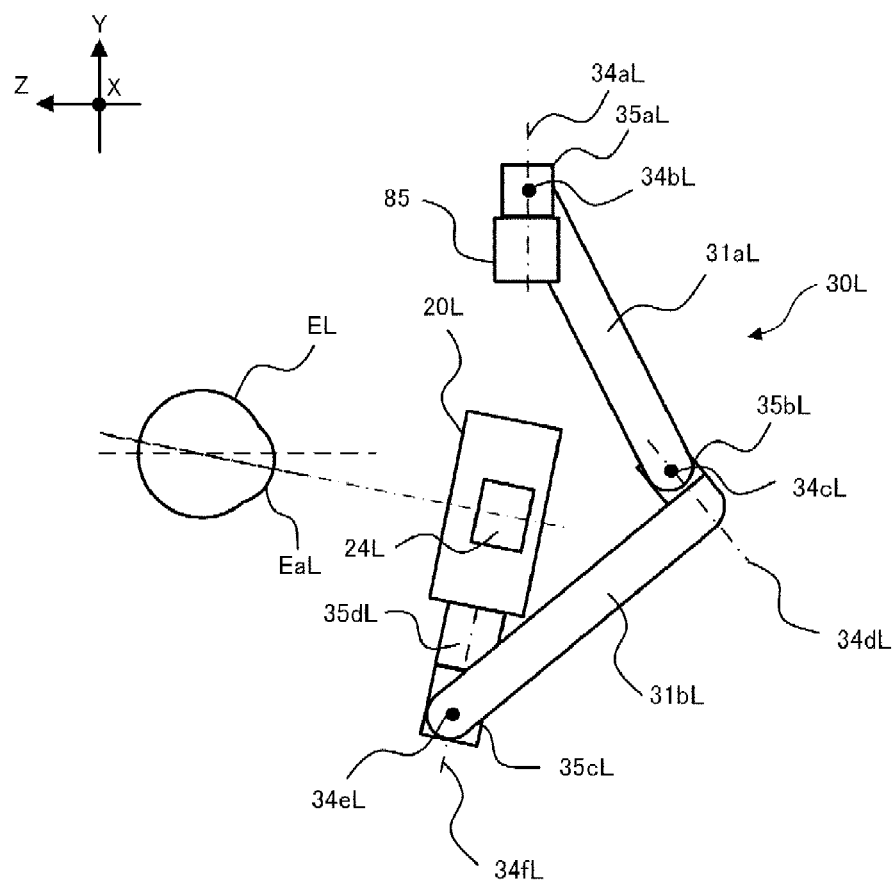
FIG. 9B is a schematic side view illustrating an operation of the head unit of the ophthalmologic apparatus according to the second embodiment of the present disclosure.

Next, referring to FIGS. 9A and 9B, it will be described below how the head unit 20L rotates in the direction of an YZ plane about the eye rotation center of the subject's eye EL. The following description is directed to the left head unit 20L and the subject's eye EL, but the same applies to the right head unit 20R and the subject's eye ER. FIGS. 9A and 9B are schematic side views illustrating the left part of the ophthalmologic apparatus 10A. FIG. 9A shows the subject's eye EL facing the front (the −Z direction). FIG. 9B shows the subject's eye EL oriented downward. In order to orient the subject's eye EL downward, a fixation target (not shown) is used to guide the gaze of the subject's eye EL. The subject's eye changes the gaze direction about the eye rotation center.

In the ophthalmologic apparatus 10A, in order to orient the gaze of the subject's eye up or down, for example, the fixation target is displayed above or below the subject's eye EL to guide the gaze. The control unit 71 controls the drive mechanism 30L to allow the head unit 20L to rotate about the eye rotation center of the subject's eye EL or the substantial eye rotation center near the eye rotation center.

Since the left and right head units 20L and 20R are respectively connected to the independent drive mechanisms 30L and 30R, the subject's left and right eyes EL and ER can be examined in directions independent from each other.

As can be seen in the foregoing, being able to freely rotate in the directions of the XZ plane and the YX plane, the left and right head units 20L and 20R can be aligned with the subject's eyes in every gaze direction, such as far, near, up, down, left and right. Further, the optical axis of the examination optical system can be independently set with respect to the subject's left and right eyes EL and ER. Thus, for example, when the subject has a heterophoria, even if the gaze direction (visual axis) of one of the subject's eyes (e.g., the subject's eye EL) meets the fixation target, the gaze direction of the other subject's eye (e.g., the subject's eye ER) deviates from the fixation target. In this case, the control unit 71 can control the orientation of the head unit 20 (e.g., the head unit 20R) based on the gaze direction of the other subject's eye (e.g., the subject's eye ER). Further, the gaze directions can be detected using the results of detection of the gaze positions of the subject's eyes EL and ER by the gaze position detection unit 73. In this way, the present disclosure can address the examination and imaging (e.g., a heterophoria test in subjective tests, and peripheral imaging in fundus photography) performed in a state where the gaze direction (visual axis) of the subject's eye is in alignment with the optical axis of the examination optical system, and a state where the gaze direction (visual axis) is not in alignment. Further, as a use example in the state where the gaze direction (visual axis) is not in alignment, an intended position can be targeted to conduct the examination while avoiding a cloudy portion of the lens of each of the left and right eyes E of the subject having a cataract.

It has been described above that each of the drive mechanisms 30L and 30R has two arms, but the number of the arms is not limited to two, and may be three or more. The six rotation support mechanisms are not necessarily required. Five or more rotation support mechanisms are sufficient, and five or more driving units will do.

Third Embodiment

A third embodiment of the present disclosure will be described below. An ophthalmologic system 1 of the third embodiment is a system that connects the ophthalmologic apparatuses 10 and 10A of the first and second embodiments to a network so that eye examination can be performed from a remote location, for example.

Figure 10:
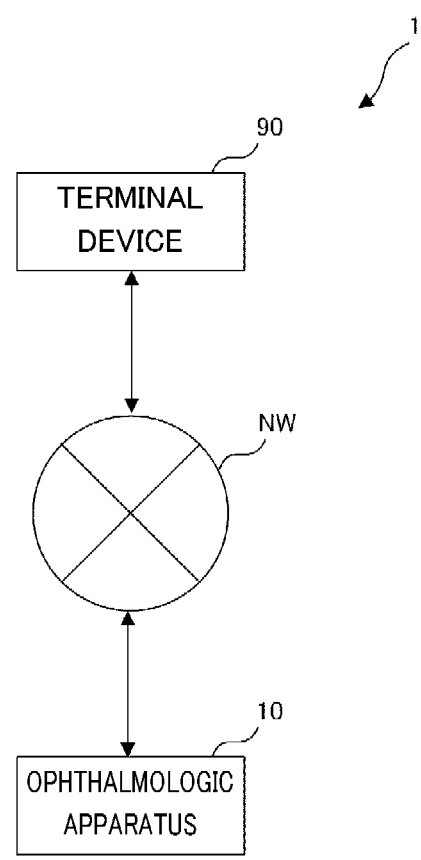
FIG. 10 is a block diagram illustrating an ophthalmologic system according to a third embodiment of the present disclosure.

FIG. 10 is a block diagram illustrating the ophthalmologic system 1 of the third embodiment. The ophthalmologic system 1 of the present embodiment is comprised of a terminal device 90 handled by a user and an ophthalmologic apparatus 10 (10A) which are connected together via a network NW such as the Internet or a virtual private network (VPN). Examples of the terminal device 90 may include a personal computer (PC), a smartphone, a tablet PC, and a mobile terminal such as a mobile phone.

The ophthalmologic system 1 of the present embodiment makes it possible to transmit examination information of the ophthalmologic apparatus 10 (10A) to the terminal device 90 via the network NW. Further, the control unit 71 may be instructed from the terminal device 90 via the network NW to control the drive mechanism 30 or any other components. As a result, for example, when a physician is physically at a distance (e.g., in a remote place) from the subject, the system can assist the physician in making a diagnosis of the subject's eye. In addition, the physician in a remote place can handle the terminal device 90 to control the drive mechanism 30 or any other components to adjust the positional relationship between the subject's eye and the head unit.

While some embodiments of the present disclosure have been described above, these embodiments may be implemented in various other forms, and various omissions, substitutions, and changes may be made without departing from the spirit of the invention. The embodiments and variations thereof are included in the scope and spirit of the invention, and are included in the invention described in the claims and their equivalents.

Note that in the above-described embodiments, the alignment is measured using a stereo camera, but this is not limiting. For example, as a possible method, the head unit may be provided with an alignment light source and a line sensor. The line sensor receives light emitted from the alignment light source and reflected from the subject's eye, and the position of the subject's eye relative to the head unit is detected based on the information from the line sensor to adjust the alignment.

What is claimed is:

1. An ophthalmologic apparatus for optically acquiring information of a subject's eye, the ophthalmologic apparatus comprising:
a head unit having an optical system capable of receiving light reflected from the subject's eye;
a drive mechanism that movably holds the head unit;
an alignment detection unit that detects a position of the subject's eye relative to the head unit; and
a control unit that controls the drive mechanism, wherein
the drive mechanism includes at least two arms rotatably connected together, at least two first rotation support mechanisms each of which is rotatable about a first axis, at least three second rotation support mechanisms each of which is rotatable about a second axis different in direction from the first axis, and at least five driving units for driving the first and second rotation support mechanisms, the first and second rotation support mechanisms allowing the head unit to move, and
the control unit is capable of controlling the driving units using a detection result of the alignment detection unit to align the head unit and the subject's eye with each other.

2. The ophthalmologic apparatus of claim 1, wherein
the at least two arms are connected together via the first rotation support mechanisms, and
the at least two arms and the head unit are connected to each other via the first rotation support mechanisms and the second rotation support mechanisms.

3. The ophthalmologic apparatus of claim 1, wherein
the first axis is capable of being oriented in a vertical direction, and the second axis is capable of being oriented in a horizontal direction orthogonal to the first axis.

4. The ophthalmologic apparatus of claim 1, wherein
the first axis is capable of being oriented in a horizontal direction, and the second axis is capable of being oriented in a vertical direction orthogonal to the first axis.

5. The ophthalmologic apparatus of claim 1, wherein
the control unit is capable of controlling the driving units to allow the head unit to move while keeping an optical axis of the optical system passing an eye rotation center of the subject's eye or a substantial eye rotation center near the eye rotation center.

6. The ophthalmologic apparatus of claim 1, wherein
the control unit is capable of controlling the driving units to align an optical axis of the optical system with a direction toward the subject's eye while maintaining a posture of the head unit.

7. The ophthalmologic apparatus of claim 1, wherein
the head unit includes two alignment cameras, and
   the alignment detection unit detects the position of the subject's eye relative to the head unit based on information of images captured by the two alignment cameras.

8. The ophthalmologic apparatus of claim 1, wherein
the head unit includes an alignment light source and a line sensor, and
the line sensor receives light emitted from the alignment light source and reflected from the subject's eye, and the alignment detection unit detects the position of the subject's eye relative to the head unit based on information from the line sensor.

9. The ophthalmologic apparatus of claim 1, wherein
the optical system includes a fundus camera capable of capturing a fundus image of the subject's eye by the light reflected from the subject's eye.

10. The ophthalmologic apparatus of claim 1, wherein
the optical system includes an anterior segment camera capable of capturing an image of an anterior segment of the subject's eye by the light reflected from the subject's eye.

11. The ophthalmologic apparatus of claim 1, further comprising a gaze position detection unit that detects a gaze position of the subject's eye, wherein
   the control unit is capable of controlling the driving units to align the head unit with the subject's eye using the gaze position detected by the gaze position detection unit.

* * * * *